US008178576B2

(12) United States Patent
Kabra et al.

(10) Patent No.: US 8,178,576 B2
(45) Date of Patent: *May 15, 2012

(54) NON-POLYMERIC LIPOPHILIC PHARMACEUTICAL IMPLANT COMPOSITIONS FOR INTRAOCULAR USE

(75) Inventors: Bhagwati P. Kabra, Arlington, TX (US); Janet D. Howie, Keller, TX (US)

(73) Assignee: Novartis AG, Basel (CH)

( * ) Notice: Subject to any disclaimer, the term of this patent is extended or adjusted under 35 U.S.C. 154(b) by 993 days.

This patent is subject to a terminal disclaimer.

(21) Appl. No.: 12/132,003

(22) Filed: Jun. 3, 2008

(65) Prior Publication Data

US 2008/0241224 A1   Oct. 2, 2008

Related U.S. Application Data

(62) Division of application No. 10/610,435, filed on Jun. 30, 2003, now Pat. No. 7,678,827.

(60) Provisional application No. 60/395,840, filed on Jul. 15, 2002.

(51) Int. Cl.
*A61F 2/00* (2006.01)

(52) U.S. Cl. ........ 514/424; 427/422; 427/424; 427/514; 427/772

(58) Field of Classification Search .................. 514/424
See application file for complete search history.

(56) References Cited

U.S. PATENT DOCUMENTS

| | | | | |
|---|---|---|---|---|
| 4,014,335 A | 3/1977 | Arnold | ........................ | 128/260 |
| 4,344,968 A | 8/1982 | Aoda et al. | | |
| 4,786,495 A | 11/1988 | Bird et al. | | |
| 4,797,288 A | 1/1989 | Sharma et al. | | |
| 4,853,224 A | 8/1989 | Wong | ........................ | 424/427 |
| 4,997,652 A | 3/1991 | Wong | ........................ | 424/428 |
| 5,015,474 A | 5/1991 | Parnell | | |
| 5,164,188 A | 11/1992 | Wong | ........................ | 424/428 |
| 5,178,635 A | 1/1993 | Gwon et al. | ..................... | 623/4 |
| 5,200,393 A | 4/1993 | Weiner | ............................. | 514/3 |
| 5,378,475 A | 1/1995 | Smith et al. | ..................... | 424/473 |
| 5,399,357 A | 3/1995 | Akiyama et al. | | |
| 5,433,951 A | 7/1995 | Serajuddin et al. | | |
| 5,443,505 A | 8/1995 | Wong et al. | ........................ | 623/4 |
| 5,466,233 A | 11/1995 | Weiner et al. | | |
| 5,629,019 A | 5/1997 | Lee et al. | ...................... | 424/489 |
| 5,632,984 A | 5/1997 | Wong et al. | ................. | 424/85.4 |
| 5,660,851 A | 8/1997 | Domb | ........................... | 424/427 |
| 5,718,922 A | 2/1998 | Herrero-Vanrell et al. | ... | 424/501 |
| 5,736,152 A | 4/1998 | Dunn | ............................. | 424/426 |
| 5,759,563 A | 6/1998 | Yewey et al. | ................. | 424/426 |
| 5,766,242 A | 6/1998 | Wong et al. | ....................... | 623/4 |
| 5,773,019 A | 6/1998 | Ashton et al. | ................. | 424/423 |
| 5,773,021 A | 6/1998 | Gurtler et al. | ................. | 424/427 |
| 5,797,898 A | 8/1998 | Santini, Jr. et al. | ........ | 604/890.1 |
| 5,824,072 A | 10/1998 | Wong | ............................ | 623/4 |
| 5,830,173 A | 11/1998 | Avery et al. | ........................ | 604/9 |
| 5,836,935 A | 11/1998 | Ashton et al. | ............. | 604/891.1 |
| 5,869,079 A | 2/1999 | Wong et al. | .................... | 424/426 |
| 5,888,533 A | 3/1999 | Dunn | ............................. | 424/423 |
| 5,891,476 A | 4/1999 | Reo et al. | | |
| 5,902,598 A | 5/1999 | Chen et al. | ..................... | 424/423 |
| 5,916,584 A | 6/1999 | O'Donoghue et al. | ........ | 424/426 |
| 6,001,386 A | 12/1999 | Ashton et al. | ................. | 424/423 |
| 6,099,853 A | 8/2000 | Hertelendy et al. | | |
| 6,110,485 A | 8/2000 | Olejnik et al. | ................. | 424/428 |
| 6,120,751 A | 9/2000 | Unger | ........................... | 424/9.51 |
| 6,120,789 A | 9/2000 | Dunn | ............................. | 424/426 |
| 6,143,276 A | 11/2000 | Unger | ............................. | 424/9.3 |
| 6,162,801 A | 12/2000 | Kita | ............................... | 514/167 |
| 6,190,691 B1 | 2/2001 | Mak | ................................ | 424/449 |
| 6,525,214 B1 | 2/2003 | Armitage et al. | | |
| 7,678,827 B2 * | 3/2010 | Kabra et al. | .................. | 514/424 |
| 2005/0020603 A1 | 1/2005 | Dai et al. | | |

FOREIGN PATENT DOCUMENTS

| | | |
|---|---|---|
| CA | 2 119 109 | 11/2002 |
| EP | 0 455 391 A2 | 11/1991 |
| EP | 0 537 165 B1 | 7/1998 |
| WO | WO 94/05257 | 3/1994 |
| WO | WO 98/40051 | 9/1998 |
| WO | WO 99/40051 | 9/1998 |
| WO | WO 01/97774 A2 | 12/2001 |
| WO | WO 01/97832 A1 | 12/2001 |
| WO | WO 03/074054 A1 | 9/2003 |

OTHER PUBLICATIONS

Compritol® 888 ATO Precirol® ATO 5, Gattefossé Product Brochure, 2001.
Gelucire®, Gattefossé Product Brochure, 1999.
Gelucire® 50/13, Gattefossé Product Brochure, 1999.
Monoglycerides, Eastman Product Brochure, 1994.
Oral Route Excipients, Gattefossé Product Brochure, 1999.
Rectal Route Excipients, Gattefossé Product Brochure, 1999.
Hamdani et al., "Physical and thermal Characterisation of Precirol® and Comptirol® as lipophlic glycerides used for the preparation of controlled-release matrix pellets." *International J. of Pharmaceutics*, vol. 260, pp. 47-57 (2003).
Witepsol and Massa Estainum disclosure downloaded from the world wide web on Nov. 19, 2007.
Mirriam-Webster disclosure "Mixture," downloaded from the world wide web on Jan. 24, 2007.
NIST disclosure "Octadecanoic acid, 2,3-dihydroxypropyl ester," downloaded from the world wide web on Jan. 24, 2007.
"Ocatadecanoic acid, monoester with triglycerol," downloaded from the world wide web Jan. 24, 2007.
Tween 80 by LC-MS downloaded from he world wide web at www.wcaslab.com/tech/Tween80.htm on May 17, 2006.
Precirol ATO 5, Gattefossé Product Brochure, one page, 2004.
Glycerol Distearate, *European Pharmacopeia*, vol. 5.0, pp. 1674-1675, 2005.
Glyceryl Distearate, *US Pharmacopeia*, pp. 3341-3342, 2007.
Glyceryl Monostearate, *Japanese Pharmacopeia*, pp. 931, 1996.
Office Action dated Sep. 10, 2010 issued by the U.S. Patent and Trademark Office for U.S. Appl. No. 11/695,990 (10 pages).

* cited by examiner

*Primary Examiner* — Jake M. Vu
(74) *Attorney, Agent, or Firm* — Kilyk & Bowersox, P.L.L.C.

(57) ABSTRACT

Solid or semi-solid intraocular implant compositions are disclosed. The compositions contain a lipophilic compound but lack a polymeric ingredient.

20 Claims, 3 Drawing Sheets

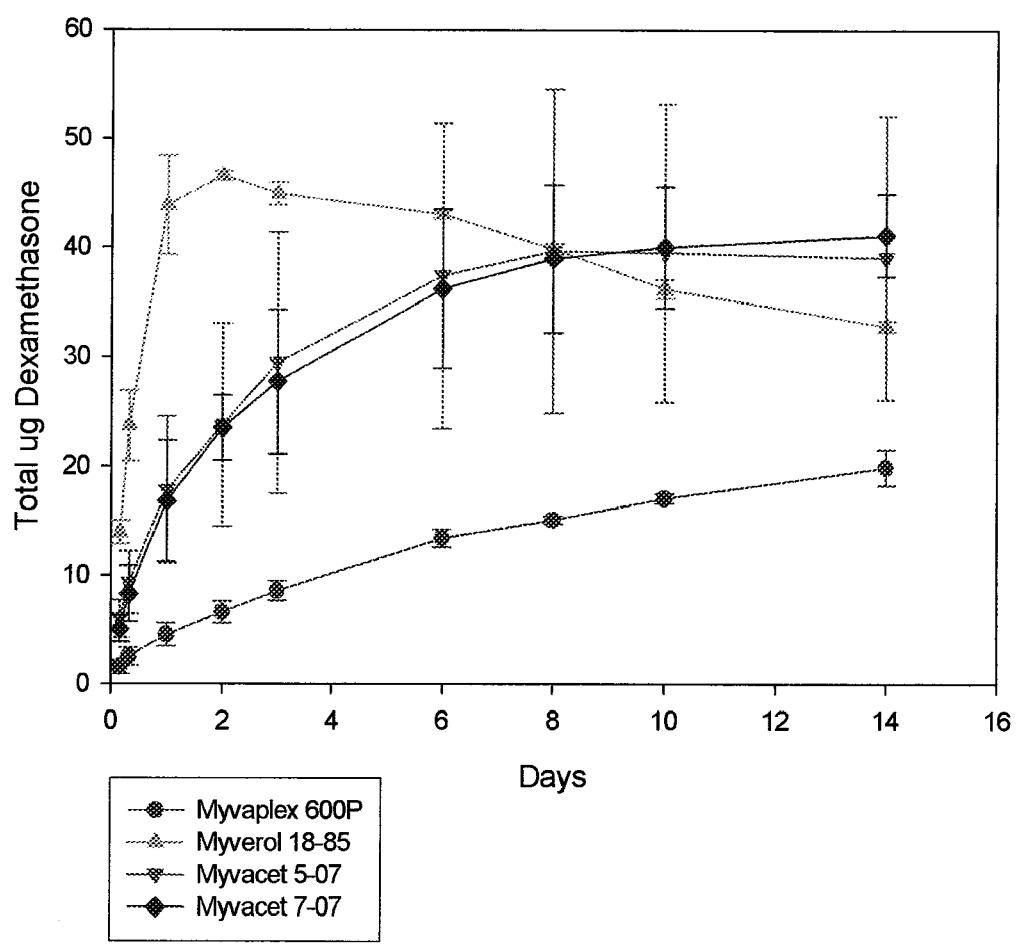
Figure 1: Release of Dexamethasone From Monoglyceride Blends (n=3)

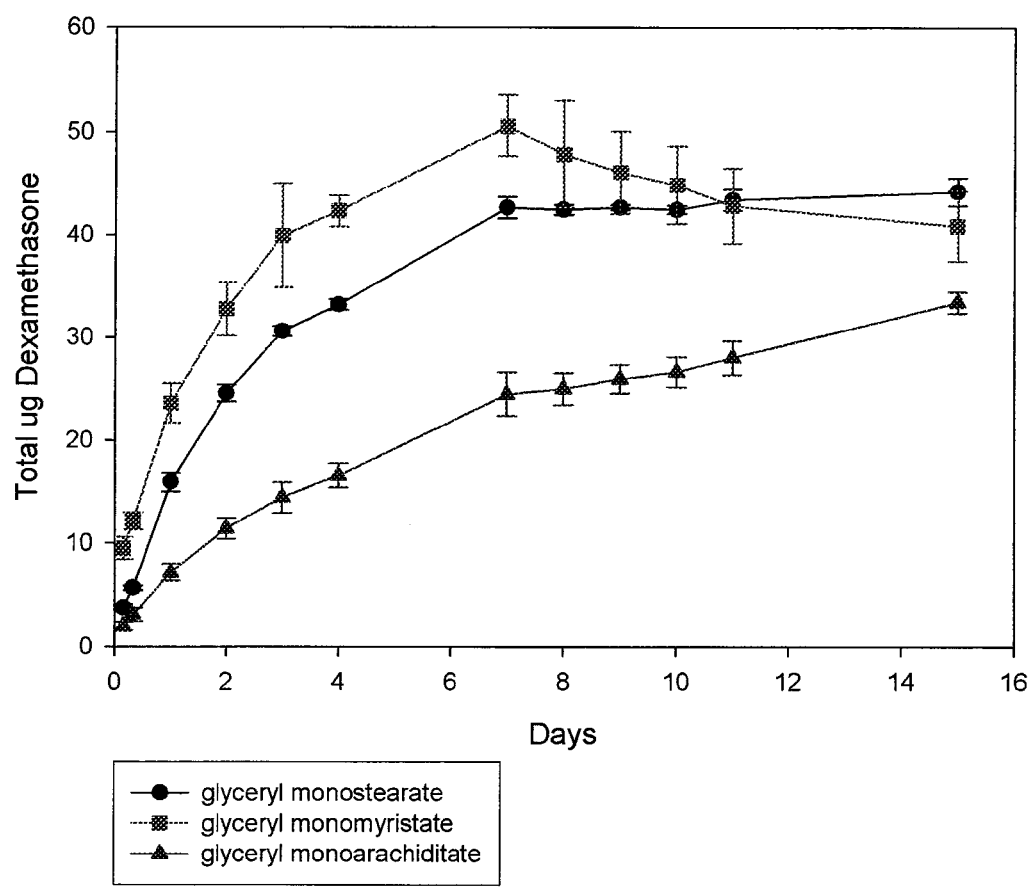
Figure 2: Release of Dexamethasone From Monoglycerides (n=3)

Figure 3: Comparison of Dexamethasone in Glyceryl Monostearate w & w/o Polysorbate 80 (n = 3)
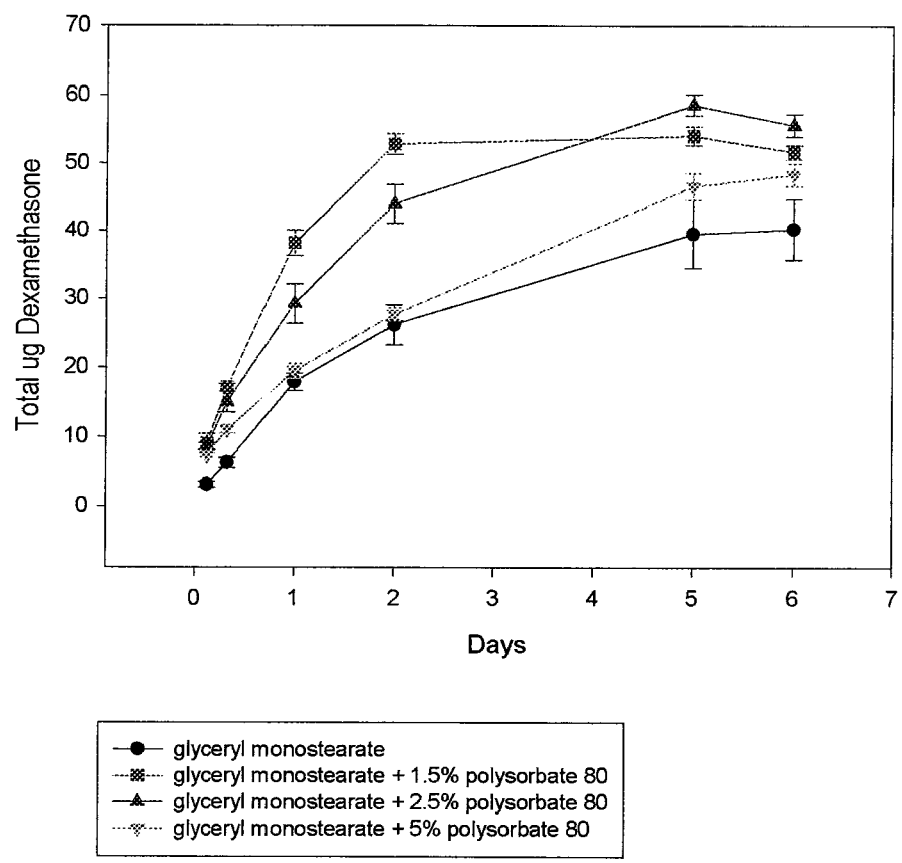

NON-POLYMERIC LIPOPHILIC PHARMACEUTICAL IMPLANT COMPOSITIONS FOR INTRAOCULAR USE

This application is a divisional of U.S. patent application Ser. No. 10/610,435, filed Jun. 30, 2003 now U.S. Pat. No. 7,678,827, which in turn claims priority to U.S. Provisional Application No. 60/395,840 filed Jul. 15, 2002, which are incorporated in their entirety by reference herein.

BACKGROUND OF THE INVENTION

This invention relates to pharmaceutical implant compositions. In particular, this invention relates to the use of low molecular weight, lipophilic compounds in implant compositions for intraocular use.

Various solid and semi-solid drug delivery implants are known, including both non-erodible, non-degradable implants, such as those made using ethylene vinyl acetate, and erodible or biodegradable implants, such as those made using polyanhydrides or polylactides. Drug delivery implants, particularly ophthalmic drug delivery implants are generally characterized by at least one polymeric ingredient. In many instances, drug delivery implants contain more than one polymeric ingredient.

For example, U.S. Pat. No. 5,773,019 discloses implantable controlled release devices for delivering drugs to the eye wherein the implantable device has an inner core containing an effective amount of a low solubility drug covered by a non-bioerodible polymer coating layer that is permeable to the low solubility drug.

U.S. Pat. No. 5,378,475 discloses sustained release drug delivery devices that have an inner core or reservoir comprising a drug, a first coating layer which is essentially impermeable to the passage of the drug, and a second coating layer which is permeable to the drug. The first coating layer covers at least a portion of the inner core but at least a small portion of the inner core is not coated with the first coating layer. The second coating layer essentially completely covers the first coating layer and the uncoated portion of the inner core.

U.S. Pat. No. 4,853,224 discloses biodegradable ocular implants comprising microencapsulated drugs for implantation into the anterior and/or posterior chambers of the eye. The polymeric encapsulating agent or lipid encapsulating agent is the primary element of the capsule. Many types of polymers are disclosed, but no implants that lack a biodegradable polymer are disclosed.

U.S. Pat. No. 5,164,188 discloses the use of biodegradable implants in the suprachoroid of an eye. The implants are generally encapsulated. The capsule, for the most part, is a polymeric encapsulating agent. Material capable of being placed in a given area of the suprachoroid without migration, "such as oxycel, gelatin, silicone, etc." can also be used.

U.S. Pat. No. 6,120,789 discloses the use of a non-polymeric composition for in situ formation of a solid matrix in an animal, and use of the composition as a medical device or as a sustained release delivery system for a biologically-active agent, among other uses. The composition is composed of a biocompatible, non-polymeric material and a pharmaceutically acceptable, organic solvent. The non-polymeric composition is biodegradable and/or bioerodible, and substantially insoluble in aqueous or body fluids. The organic solvent solubilizes the non-polymeric material, and has a solubility in water or other aqueous media ranging from miscible to dispersible. When placed into an implant site in an animal, the non-polymeric composition eventually transforms into a solid structure. The implant can be used for treating a tissue defect by enhancing cell growth and tissue regeneration, wound and organ repair, nerve regeneration, soft and hard tissue regeneration, and the like. The composition can include a biologically-active agent (bioactive agent), as for example, an anti-inflammatory agent, an antiviral agent, antibacterial or antifungal agent useful for treating and preventing infections in the implant site, a growth factor, a hormone, and the like. The resulting implant provides a system for delivering the biologically-active agent to the animal. According to the '789 patent, suitable organic solvents are those that are biocompatible, pharmaceutically acceptable, and will at least partially dissolve the non-polymeric material. The organic solvent has a solubility in water ranging from miscible to dispersible. The solvent is capable of diffusing, dispersing, or leaching from the composition in situ into aqueous tissue fluid of the implant site such as blood serum, lymph, cerebral spinal fluid (CSF), saliva, and the like. According to the '789 patent, the solvent preferably has a Hildebrand (HLB) solubility ratio of from about 9-13 $(cal/cm^3)^{1/2}$ and it is preferred that the degree of polarity of the solvent is effective to provide at least about 5% solubility in water.

Polymeric ingredients in erodible or biodegradable implants must erode or degrade in order to be transported through ocular tissues and eliminated. Low molecular weight molecules, on the order of 4000 or less, can be transported through ocular tissues and eliminated without the need for biodegradation or erosion.

SUMMARY OF THE INVENTION

The present invention provides intraocular implant compositions comprising one or more low molecular weight lipophilic compounds and a pharmaceutical drug, but lacking a polymeric ingredient and an organic solvent that is miscible with or dispersible in water. The compositions are solid or semi-solid at temperatures $\leq 37°$ C., average human eye temperature. The implants can be placed anywhere in the eye, including the conjunctival cul-de-sac, but are especially suitable for implantation inside of the eye.

BRIEF DESCRIPTION OF THE DRAWINGS

FIG. 1 shows the release of dexamethasone from implant compositions containing the indicated monoglyceride blends.

FIG. 2 shows the release of dexamethasone from implant compositions containing the indicated monoglycerides.

FIG. 3 shows the release of dexamethasone from implant compositions containing glyceryl monostearate and a varying amount of surfactant.

DETAILED DESCRIPTION OF THE INVENTION

Unless indicated otherwise, all ingredient amounts expressed in percentage terms are presented as % w/n.

As used herein, "implant" means a solid or semi-solid mass that contains one or more drugs and includes, but is not limited to, beads, pellets, rods, films and microparticles. Microparticles can be suspended in aqueous or nonaqueous liquid carriers.

The implant compositions of the present invention, which lack both a polymeric ingredient and an organic solvent that is miscible with or dispersible in water, comprise a pharmaceutical drug and one or more lipophilic compounds having a molecular weight of 150-4000, wherein the lipophilic compounds are of
the formula:

(I)

wherein
R$^1$ is —H, —OH, —COOH, —C$_n$H$_{2n+1-2m}$, —COOC$_n$H$_{2n+1-2m}$, —COO(CH$_2$CH$_2$O)$_n$CH$_2$CH$_2$OH, —CH$_2$R$^3$, or

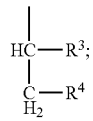

R$^2$, R$^3$ and R$^4$ are independently —H, —OH, —COOH, —C$_n$H$_{2n+1-2m}$, —OOCC$_n$H$_{2n+1-2m}$, —COOC$_n$H$_{2n+1-2m}$, —COO(CH$_2$CH$_2$O)$_n$CH$_2$CH$_2$OH, —C$_n$H$_{2n+1-2m}$COO(CH$_2$CH$_2$O)$_n$CH$_2$CH$_2$OH, —OOCC$_n$H$_{2n+1-2m}$COOC$_n$H$_{2n+1-2m'}$, —COO$^-$Na$^+$, —COO$^-$K$^+$, —SO$_3$H, —SO$_3^-$Na$^+$, —SO$_3^-$K$^+$, —NH$_2$, —Cl,

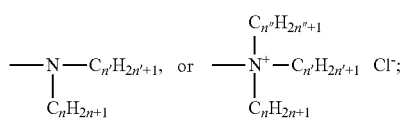

n, n' and n" are independently 0-50; and
m, m' and m" are independently 0-10.

Preferably, the molecular weight of the lipophilic compounds used in the present invention is ≦2000, and most preferably ≦1000. If the implant of the present invention contains only one lipophilic compound of formula (I), then the lipophilic compound must have a melting point ≧34° C., preferably ≧37° C. If the implant contains two or more lipophilic compounds of formula (I), it is only necessary that the mixture has a melting point ≧34° C., and preferably ≧37° C. The lipophilic compounds are water-insoluble at 37° C. (i.e., have a solubility in water of <0.5 mg/ml at 37° C.).

Preferred are the lipophilic compounds of formula (I) wherein
R$^1$ is, —C$_n$H$_{2n+1-2m}$, —COOC$_n$H$_{2n+1-2m}$, —COO(CH$_2$CH$_2$O)$_n$CH$_2$CH$_2$OH, —CH$_2$R$^3$, or

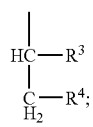

R$^2$, R$^3$ and R$^4$ are independently —H, —OH, —COOH, —C$_n$H$_{2n+1-2m}$, —OOCC$_n$H$_{2n+1-2m}$, —COOC$_n$H$_{2n+1-2m}$, —COO(CH$_2$CH$_2$O)$_n$CH$_2$CH$_2$OH, —C$_n$H$_{2n+1-2m}$COO(CH$_2$CH$_2$O)$_n$CH$_2$CH$_2$OH, or —OOCC$_n$H$_{2n+1-2m}$COOC$_n$H$_{2n+1-2m'}$,
n, n' and n" are independently 0-40; and
m, m' and m" are independently 0-5.

Most preferred are the lipophilic compounds of formula (I) wherein
R$^1$ is

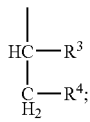

R$^2$, R$^3$ and R$^4$ are independently —H, —OH, —COOH, —C$_n$H$_{2n+1-2m}$, or —OOCC$_n$H$_{2n+1-2m}$,
n, n' and n" are independently 0-30; and
m, m' and m" are independently 0-3.

Especially preferred lipophilic compounds of formula (I) are glyceryl monolaurate; glyceryl dilaurate; glyceryl monomyristate; glyceryl dimyristate; glyceryl monopalmitate; glyceryl dipalmitate; glyceryl monostearate; glyceryl distearate; glyceryl monooleate; glyceryl dioleate; glyceryl monolinoleate; glyceryl dilinoleate; glyceryl monoarachidate; glyceryl diarachidate; glyceryl monobehenate; and glyceryl dibehenate.

As used herein, "an organic solvent miscible with or dispersible in water" means an organic solvent that is biocompatible, pharmaceutically acceptable, and has a solubility in water ranging from miscible to dispersible. These organic solvents that are excluded from the compositions of the present claims are the same as those that are essential in the compositions described in U.S. Pat. No. 6,120,789.

The lipophilic compounds of the present invention can be made by methods known in the art and many such compounds are commercially available. For example, commercial suppliers include NuChek Prep (Elysian, Minn.), Quest International (Hoffman Estates, Ill.), which produces such compounds under the Myvaplex® and Myvacet® brands, and Gattefossa (Saint-Priest, France), which produces such compounds under the Gelucire® and Geleol® brands. Suitable lipophilic compounds include, but are not limited to, the following commercially available products.
diethylene glycol monostearate (Hydrine®; m.p.=45.5-48.5° C.);
propylene glycol mono- and diesters of stearic and palmitic acid (Monosteol®; m.p.=34.0-37.5° C.; 'propylene glycol monostearate');
glyceryl monostearate (Geleol®; m.p.=70° C.);
glyceryl monolinoleate (Maisine®35-1; m.p.=−6.5° C.);
glyceryl monooleate (Peceol®; m.p.=16° C.);
the mixture of monoglycerides sold as Myverol® 18-85 (m.p.=46° C.);
the mixture of glyceryl monostearate (85-90%) and glyceryl monopaimitate (10-15%) (Myvaplex® 600 P; m.p.=69° C.);
glyceryl esters of saturated C$_{12}$-C$_{18}$ saturated fatty acid esters (Gelucire® 43/01; m.p.=42-46° C.);
glyceryl esters of saturated C$_8$-C$_{18}$ saturated fatty acid esters (Gelucire® 33/01; m.p.=33-37° C.); and
glyceryl esters of saturated C$_{12}$-C$_{18}$ saturated fatty acid esters (Gelucire® 39/01; m.p.=37.5-41° C.); and The implant compositions of the present invention comprise one or more lipophilic compounds of formula (I) in a total concentration of at least 10%, preferably at least 30%, and most preferably at least 50%.

The implant compositions of the present invention comprise a pharmaceutically effective amount of an ophthalmic drug. If necessary or desired, more than one drug can be included in the implant of the present invention. Many types of ophthalmic drugs are known, including but not limited to: anti-glaucoma agents, such as beta-blockers including timolol, betaxolol, levobetaxolol, carteolol, miotics including pilocarpine, carbonic anhydrase inhibitors, prostaglandin analogues, seretonergics, muscarinics, dopaminergic agonists, adrenergic agonists including apraclonidine and brimonidine; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone, dexamethasone and tetrahydrocortisol; growth factors, such as VEGF; immunosuppressant agents; neuroprotectant agents; angiogenesis-inhibiting agents and anti-allergy agents including olopatadine. The ophthalmic drug may be present in the form of a pharmaceutically acceptable salt, such as timolol maleate, brimonidine tartrate or sodium diclofenac. Compositions of the present invention may also include combinations of ophthalmic drugs, such as combinations of (i) a beta-blocker selected from the group consisting of betaxolol and timolol, and (ii) a prostaglandin selected from the group consisting of latanoprost; 15-keto latanoprost; fluprostenol isopropyl ester (especially 1R-[1α(Z),2β(1E, 3R*),3α,5α]-7-[3,5-dihydroxy-2-[3-hydroxy-4-[3-(trifluoromethyl)-phenoxy]-1-butenyl]cyclo-pentyl-]-5-heptenoic acid, 1-methylethyl ester); isopropyl[2R(1E,3R),3S(4Z), 4R]-7-[tetrahydro-2-[4-(3-chlorophenoxy)-3-hydroxy-1-butenyl]-4-hydroxy-3-furanyl]-4-heptenoate; and (5Z)-(9R, 11R,15R)-9-chloro-15-cyclohexyl-11,15-dihydroxy-3-oxa-16,17,18,19,20-pentanor-5-prostenoic acid isopropyl ester. The total amount of drug contained in the implant compositions of the present invention is preferably not greater than 50%.

In addition to the lipophilic compound of formula (I) and an ophthalmic drug, the implant compositions of the present invention optionally comprise one or more excipients. Many excipients for solid and semi-solid pharmaceutical compositions are known. Examples of suitable excipients include, but are not limited to: surfactants, preservatives, and stabilizers.

Suitable surfactants include tyloxapol, polysorbate 20, polysorbate 60, and polysorbate 80 surfactants. A preferred surfactant is polysorbate 80.

Suitable preservatives include quaternary ammonium preservatives such as polyquaternium-1 and benzalkonium halides. Preferred benzalkonium halides are benzalkonium chloride ("BAC") and benzalkonium bromide.

Suitable stabilizers include chelating agents, such as edetate disodium, and antioxidants, such as ascorbic acid and citric acid.

The implant compositions may be fashioned into a shape suitable for implantation into the eye. For example, such shapes include, but are not limited to cylindrical, conical and spherical shapes. Alternatively, the implant compositions may be of a shape and size such that they may be suspended in a liquid carrier and injected or deposited into the eye. The size and shape of the implant of the present invention will depend on a number of factors, including the selected drug, the target disease and the selected implant location. The implants of the present invention may be implanted anywhere in the eye, including the conjunctival cul-de-sac, punctum and lacrimal canaliculus, anterior and posterior segments, and the sub-Tenon's, suprachoroidal and subconjunctival spaces.

Although the implant compositions are preferably administered as a solid or semi-solid, in one embodiment the composition is warmed and administered in a semi-solid or liquid state through a cannula. After cooling to body temperature at the site of administration, the composition will form a semi-solid or solid implant.

The following examples are intended to illustrate, but not limit, the present invention.

Example 1

Placebo Pellets 0.25 g of polysorbate 80 and 4.75 g of the monoglyceride Myverol 18-35 were added to a scintillation vial. The monoglyceride was melted by heating in a water bath. The polysorbate 80 and monoglyceride were then mixed by swirling. Pellets were made by cooling the solution in a cylindrical mold. This procedure was repeated for the monoglycerides Myverol 18-50, Myverol 18-85, and Myaplex 600P.

In order to illustrate the relationship between the exemplified materials and formula (I), Myverol 18-35, Myverol 18-50 and Myverol 18-85 contain, according to their manufacturer, the following ingredients in the proportions shown:

|  | Monoglyceride Ingredient | Abbreviation | Wt. % |
|---|---|---|---|
| a) Myverol 18-35 | glyceryl monolaurate | C12.0 | 0.3 |
|  | glyceryl monomyristate | C14.0 | 1.1 |
|  | glyceryl monopalmitate | C16.0 | 44.1 |
|  | glyceryl monostearate | C18.0 | 4.5 |
|  | glyceryl monooleate | C18.1 | 39.3 |
|  | glyceryl monolinoleate | C18.2 | 10.2 |
|  | glyceryl monoarachidate | C20.0 | 0.3 |
| b) Myverol 18-50 | glyceryl monomyristate | C14.0 | 0.1 |
|  | glyceryl monopalmitate | C16.0 | 10.8 |
|  | glyceryl monostearate | C18.0 | 12.6 |
|  | glyceryl monooleate | C18.1 | 73.9 |
|  | glyceryl monolinoleate | C18.2 | 1.9 |
|  | glyceryl monoarachidate | C20.0 | 0.3 |
|  | glyceryl monobehenate | C22.0 | 0.3 |
| c) Myverol 18-85 | glyceryl monomyristate | C14.0 | 0.8 |
|  | glyceryl monopalmitate | C16.0 | 22.3 |
|  | glyceryl monostearate | C18.0 | 2.5 |
|  | glyceryl monooleate | C18.1 | 17.6 |
|  | glyceryl monolinoleate | C18.2 | 54.8 |
|  | glyceryl monoarachidate | C20.0 | 0.3 |
|  | glyceryl monobehenate | C22.0 | 0.3 |

C18.0 represents the compound:

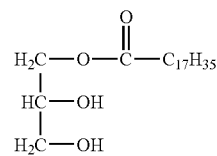

C18.1 represents the compound:

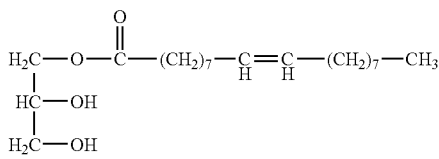

C18.2 represents the compound:

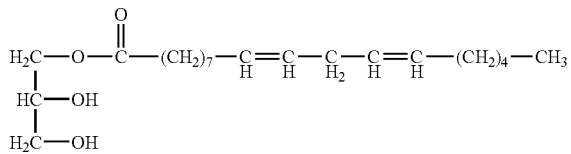

Example 2

Implant Compositions Containing Dexamethasone

1×3 mm cylindrical pellets of the formulations shown in Table 1 below were prepared by combining the indicated ingredients in a scintillation vial, melting the lipophilic compound(s) of formula (I) by heating in a water bath, mixing by swirling, and then cooling the mixed, melted formulations in cylindrical molds.

TABLE 1

Formulations

| Formulation # | Compound(s) of Formula (I) | Dexamethasone wt. % | Polysorbate 80 wt. % | Figure # |
|---|---|---|---|---|
| 1 | Myvaplex 600P | 3.5 | None | 1 |
| 2 | Myverol 18-85 | 3.5 | None | 1 |
| 3 | Myvacet 5-07 | 3.5 | 1.5 | 1 |
| 4 | Myvacet 7-07 | 3.5 | 1.5 | 1 |
| 5 | Glyceryl Monostearate | 3.5 | None | 2 |
| 6 | Glyceryl Monomyristate | 3.5 | None | 2 |
| 7 | Glyceryl Monobehenitate | 3.5 | None | 2 |
| 8 | Glyceryl Monostearate | 3.5 | None | 3 |
| 9 | Glyceryl Monostearate | 3.5 | 1.5 | 3 |
| 10 | Glyceryl Monostearate | 3.5 | 2.5 | 3 |
| 11 | Glyceryl Monostearate | 3.5 | 5 | 3 |

The release of dexamethasone from each formulation shown in Table 1 was measured by placing one pellet in a 2 ml vial containing 1.5 ml of phosphate buffered saline. Phosphate buffered saline ("PBS") contains 0.8% NaCl, 0.12% $Na_2HPO_4$, and 0.06% $NaH_2PO_4:H_2O$. The vial is then placed in an oven at 37° C.

At each time point, the vial is gently inverted twice, 60 μl of the PBS is removed from the vial for HPLC analysis of dexamethasone, 60 μl of fresh PBS is added to the vial, and the vial placed back into the oven until the next time point. Each formulation is run in triplicate. The results are shown in FIGS. 1-3.

Example 3

Implant Compositions Formulated as Particles Suspended in a Liquid Carrier

A 75:20:5 mixture of anecortave acetate powder, glyceryl monostearate and polysorbate 80 is heated to melt the glyceryl monostearate and mixed. This mixture is then spray dried to produce particles. The particles are then suspended in an aqueous vehicle comprising sodium chloride, sodium dibasic phosphate, sodium monobasic phosphate, carboxymethyl cellulose and tyloxapol to produce a composition suitable for injection.

Example 4

Implant Compositions Warmed Before Administration and Injected Through a Cannula A 50:45:5 mixture of anecortave acetate powder, Gelucire 39/01 (glycerol esters of saturated C12-C18 saturated fatty acid esters are heated to melt the Gelucire 39/01 and mixed. Before injection, this composition is heated to about 41° C. and is drawn in a syringe. It is then injected through a cannula in the sub-tenon's space. Upon cooling to 37° C., it forms a solid waxy mass.

Example 5

Implant Composition Containing 80 μg of a Prostaglandin

Two 1 μl-sized cylindrical pellets each containing 80 μg of the prostaglandin analogue (5Z)-(9R,11R,15R)-9-chloro-15-cyclohexyl-11,15-dihydroxy-3-oxa-16,17,18,19,20-pentanor-5-prostenoic acid isopropyl ester were prepared by combining the prostaglandin analogue with the necessary amount of the product Precirol® ATO 5 (Gattefossa) in a scintillation vial, melting the lipophilic compounds by heating in a water bath, mixing by swirling, and then cooling the mixed, melted formulations in cylindrical molds. According to the manufacturer, Precirol® ATO 5 is composed of mono-, di- and triglycerides of palmitostearic acid, with the diester fraction being predominant. Precirol® ATO 5 is synthesized by esterification of glycerol by palmitostearic acid.

The release of the prostaglandin analogue from the pellets was measured as follows: after weighing, the pellets were placed in scintillation vials with 20 ml of PBS. The vials were stored in a 37° C. oven. At each time point the vial was gently inverted a few times (about 5 times), then 300 μl of the dissolution sample was removed from the vial and the vial returned to the oven. The amount of prostaglandin analogue contained in the sample was determined by HPLC analysis. The results are shown in Table 2.

TABLE 2

| Time (days) | Cumulative Drug Release (μg) | | Cumulative Drug Release (% of initial 80 μg) | |
|---|---|---|---|---|
| 1 | 1.70 | 1.84 | 2.18 | 2.17 |
| 3 | 28.6 | 32 | 36.67 | 37.65 |
| 8 | 73 | 76.6 | 93.59 | 90.12 |
| 11* | 65 | 69.4 | 83.33 | 81.65 |

*Drug may be degrading in the dissolution medium.

Example 6

Implant Composition Containing 200 μg of a Prostaglandin

Two 3 μl-sized cylindrical pellets each containing 200 μg of (5Z)-(9R,11R,15R)-9-chloro-15-cyclohexyl-11,15-dihydroxy-3-oxa-16,17,18,19,20-pentanor-5-prostenoic acid isopropyl ester were prepared by combining the prostaglandin analogue with the necessary amount of the product Compritol® 888 ATO (Gattefossa) in a scintillation vial, melting the lipophilic compounds by heating in a water bath, mixing by swirling, and then cooling the mixed, melted formulations in cylindrical molds. According to the manufacturer, Compritol® 888 ATO is composed of mono-, di- and triglycerides of behenic acid, with the diester fraction being predominant. Compritol® 888 ATO is synthesized by esterification of glycerol by behenic acid.

The release of the prostaglandin analogue from the pellets was measured as follows: after weighing, the pellets were placed in scintillation vials with 20 ml of PBS. The vials were stored in a 37° C. oven. At each time point, the vial was gently inverted a few times (about 5 times), then 300 μl of the dissolution sample was removed from the vial and the vial returned to the oven. The amount of prostaglandin analogue contained in the sample was determined by HPLC analysis. The results are shown in Table 3.

TABLE 3

| Time (days) | Cumulative Drug Release (μg) | | Cumulative % Drug Release (% of initial 80 μg) | |
|---|---|---|---|---|
| 1 | 12.18 | 11.38 | 5.37 | 4.78 |
| 3 | 3.32 | 3.02 | 1.46 | 1.27 |
| 8 | 12.1 | 14.04 | 5.33 | 5.90 |
| 11 | 25.6 | 31 | 11.28 | 13.03 |
| 15 | 52.6 | 66.4 | 23.17 | 27.90 |
| 22 | 54.6 | 102.4 | 24.05 | 43.03 |
| 30 | 88.8 | 107.4 | 39.12 | 45.13 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of delivering an ophthalmically acceptable drug to the eye comprising the steps of
   (a) preparing an intraocular implant composition comprising a lipophilic compound having a molecular weight of 150-4000 and a pharmaceutically effective amount of a drug, but lacking a polymeric ingredient and an organic solvent that is miscible with or dispersible in water, wherein the composition is solid or semi-solid at a temperature of 37° C. or less and the lipophilic compound is of the formula

(I)

wherein
$R^1$ is —H, —OH, —COOH, —$C_nH_{2n+1-2m}$, —COO$C_nH_{2n+1-2m}$, —COO(CH$_2$CH$_2$O)$_n$CH$_2$CH$_2$OH, —CH$_2R^3$, or

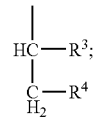

$R^2$, $R^3$ and $R^4$ are independently —H, —OH, —COOH, —$C_nH_{2n+1-2m}$, —OOC$C_nH_{2n+1-2m}$, —COO$C_nH_{2n+1-2m}$, —COO(CH$_2$CH$_2$O)$_n$CH$_2$CH$_2$OH, —$C_nH_{2n+1-2m}$COO(CH$_2$CH$_2$O)$_n$CH$_2$CH$_2$OH, —OOC$C_nH_{2n+1-2m}$COO$C_nH_{2n'+1-2m'}$, —COO$^-$Na$^+$, —COO$^-$Na$^+$, —COO$^-$K$^+$, —SO$_3$H, —SO$_3^-$Na$^+$, —SO$_3^-$K$^+$, —NH$_2$, —Cl,

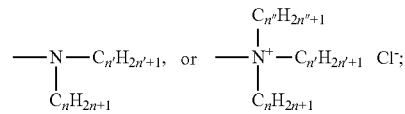

n, n' and n" are independently 0-50; and
m, m' and m" are independently 0-10;
and
   (b) implanting the composition prepared in step (a) in the eye.

2. The method of claim 1 wherein in step (b) the composition prepared in step (a) is implanted in a site selected from the group consisting of the conjunctival cul-de-sac; punctum; lacrimal canaliculus; anterior segment; posterior segment; sub-Tenon's space; suprachoroidal space; and subconjunctival space.

3. The method of claim 1 wherein the composition is warmed to a temperature above room temperature and administered through a cannula.

4. The method of claim 1 wherein the composition is administered as a solid or semi-solid.

5. The method of claim 1 wherein the intraocular implant composition of step (a) is suspended in a liquid carrier and implanted in the eye in step (b) by administration through a cannula.

6. The method of claim 1, wherein the composition is solid or semi-solid at temperatures ≦34° C.

7. The method of claim 1, wherein the molecular weight of the lipophilic compound of formula (I) is ≦2000.

8. The method of claim 1, wherein the molecular weight of the lipophilic compound of formula (I) is ≦1000.

9. The method of claim 1, wherein the composition comprises a mixture of two or more lipophilic compounds of formula (I).

10. The method of claim 1, wherein the lipophilic compound of formula (I) has a melting point >37° C.

11. The method of claim 1, wherein at least one lipophilic compound of formula (I) has a melting point <37° C. but the composition has a melting point >37° C.

12. The method of claim 1, wherein $R^1$ is, $-C_nH_{2n+1-2m}$, $-COOC_nH_{2n+1-2m}$, $-COO(CH_2CH_2O)_nCH_2CH_2OH$, $-CH_2R^3$, or

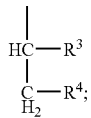

$R^2$, $R^3$ and $R^4$ are independently $-H$, $-OH$, $-COOH$, $-C_nH_{2n+1-2m}$, $-OOCC_nH_{2n+1-2m}$; $-COOC_nH_{2n+1-2m}$, $-COO(CH_2CH_2O)_nCH_2CH_2OH$, $-C_{n-}H_{2n+1-2m}COO(CH_2CH_2O)_nCH_2CH_2OH$, or $-OOCC_nH_{2n+1-2m}COOC_nH_{2n'+1-2m'}$;
n and n' are independently 0-40; and
m and m' are independently 0-5.

13. The method of claim 1, wherein $R^1$ is

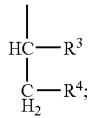

$R^2$, $R^3$ and $R^4$ are independently $-H$, $-OH$, $-COOH$, $-C_nH_{2n+1-2m}$, or $-OOCC_nH_{2n+1-2m}$;
n is independently 0-30; and
m is independently 0-3.

14. The method of claim 1, wherein said lipophilic compound is present in an amount of at least 50 wt % based on the weight of the intraocular implant composition, and wherein the lipophilic compound of formula (I) is diethylene glycol monostearate; propylene glycol monostearate; glyceryl monostearate; glyceryl monolinoleate; glyceryl monooleate; or glyceryl monopalmitate; or any mixture thereof.

15. The method of claim 1, wherein said lipophilic compound is present in an amount of at least 50 wt % based on the weight of the intraocular implant composition, and wherein the lipophilic compound of formula (I) is glyceryl monolaurate; glyceryl dilaurate; glyceryl monomyristate; glyceryl dimyristate; glyceryl monopalmitate; glyceryl dipalmitate; glyceryl monostearate; glyceryl distearate; glyceryl monooleate; glyceryl dioleate; glyceryl monolinoleate; glyceryl dilinoleate; glyceryl monoarachidate; glyceryl diarachidate; glyceryl monobehenate; or glyceryl dibehenate.

16. The method of claim 1, wherein the composition comprises at least 10% (wt.) of the lipophilic compound of formula (I).

17. The method of claim 1, wherein the composition comprises at least 30% (wt.) of the lipophilic compound of formula (I).

18. The method of claim 1, wherein the composition comprises at least 50% (wt.) of the lipophilic compound of formula (I).

19. The method of claim 1, wherein the drug is an anti-glaucoma agent; anti-infective agent; non-steroidal and steroidal anti-inflammatory agent; growth factor; immunosuppressant agent; neuroprotectant agent; angiogenesis-inhibiting agent or anti-allergy agent.

20. The method of claim 1, wherein the composition further comprises one or more excipients selected from the group consisting of surfactants, preservatives, and stabilizers.

* * * * *